United States Patent [19]
Bianchetti

[11] Patent Number: 6,095,810
[45] Date of Patent: *Aug. 1, 2000

[54] DENTAL HAND INSTRUMENT WITH INCORPORATED LIGHT SOURCE FOR DIAGNOSTIC PURPOSES

[75] Inventor: Fernando Bianchetti, Chiavari, Italy

[73] Assignee: Mectron S.r.l., Carasco, Italy

[ * ] Notice: This patent is subject to a terminal disclaimer.

[21] Appl. No.: 09/178,185

[22] Filed: Oct. 23, 1998

[30] Foreign Application Priority Data

Nov. 10, 1997 [IT] Italy ................................ MI97A2502

[51] Int. Cl.[7] .................................................. A61C 1/00
[52] U.S. Cl. ............................................. 433/29; 433/118
[58] Field of Search ........................... 433/29, 118, 119

[56] References Cited

U.S. PATENT DOCUMENTS

| | | | |
|---|---|---|---|
| 3,109,238 | 11/1963 | Marks | 433/29 |
| 4,184,196 | 1/1980 | Moret et al. | 433/29 |
| 4,634,376 | 1/1987 | Mossle et al. | 433/29 |
| 4,634,379 | 1/1987 | Mossle et al. | 433/29 |
| 4,642,738 | 2/1987 | Meller | 363/119 |
| 4,840,563 | 6/1989 | Altendorf | 433/98 |

FOREIGN PATENT DOCUMENTS

| | | | |
|---|---|---|---|
| 0 192 415 | 8/1986 | European Pat. Off. | |
| 2 563 992 | 11/1985 | France. | |
| 3328603 | 2/1985 | Germany | 433/29 |
| 37 39 009 | 9/1988 | Germany. | |
| 3706934 | 9/1988 | Germany | 433/29 |
| 40 32 779 | 4/1992 | Germany. | |

Primary Examiner—John J. Wilson
Attorney, Agent, or Firm—Chernoff, Vilhauer, McClung & Stenzel, LLP

[57] ABSTRACT

A dental hand instrument consisting of a body (1) destined to be coupled at one end with a cover (14) and at the other end with an electrical and hydraulic connector (4); inside said body (1) is positioned a transducer (2) destined to vibrate a workpiece (10) which effects removal of tartar and plaque from the tooth surface, wherein within the body of the handpiece a light source is disposed that emits blue light, able to detect tartar and plaque in the areas in which to operate, treated beforehand with a contrast agent.

8 Claims, 3 Drawing Sheets

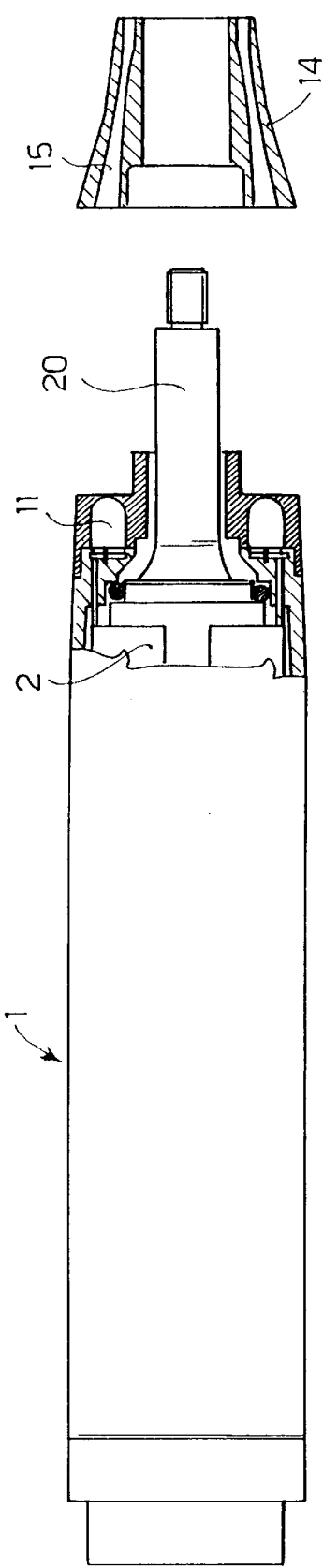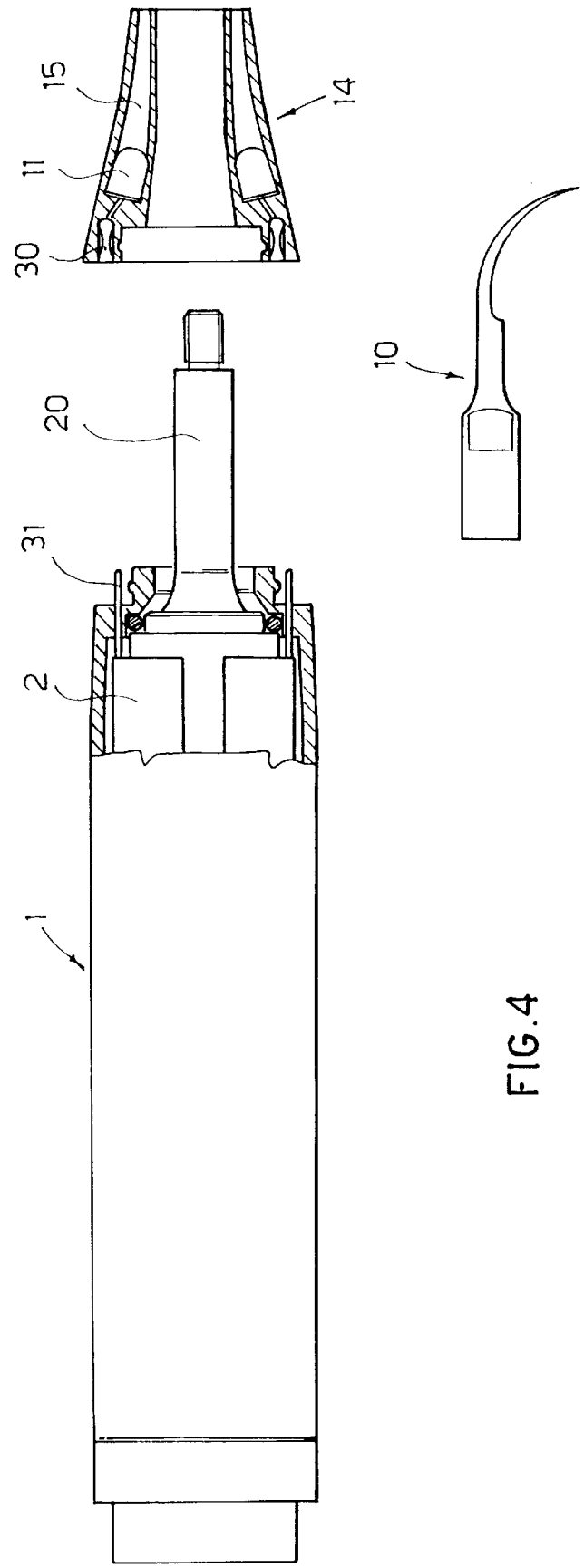
FIG. 2
FIG. 4

DENTAL HAND INSTRUMENT WITH INCORPORATED LIGHT SOURCE FOR DIAGNOSTIC PURPOSES

BACKGROUND AND SUMMARY OF THE INVENTION

The present invention refers to a dental hand instrument having a light source for diagnostic purposes.

The invention refers in particular to a surgical instrument employed by dentists for scaling and removing tartar and plaque from the tooth surface, commonly called a hand instrument, provided with a light source for illuminating the working area in the patient's oral cavity.

The hand instrument is provided with a transducer that serves to vibrate a hooked instrument called a workpiece that provides for removal of tartar from the tooth surface. Said workpiece has a through hole wherefrom a cleaning fluid which aids the cleaning operation on oral cavity can be discharged.

Plaque is a deposit of bacteria that forms through lack of hygiene or disease of the oral cavity; if it is not removed plaque creates the formation of tartar which is a calculus that forms on the tooth surface. The methods commonly used to identify plaque entail administering a plaque-revealing contrast agent to the patient in the form of liquid rinses or chewable tablets. Said contrast agent, of a neutral colour specifically not to stain the mouth, is partly absorbed by the tartar and is sensitive to blue light with which it reacts assuming a certain colour.

The next operation therefore consists in illuminating the patient's oral cavity with a blue light to identify the areas of plaque which assume a more marked colour and can therefore be better identified.

The hand instrument is subsequently used for removal of the tartar and plaque through vibration of the workpiece and spraying of the liquid.

Different types of hand instruments are currently known to the art. All the known hand instrument use iodine filament lamps which emit white light as their light sources. This is due to the fact that the problem of illuminating the working area in the oral cavity has been taken into greater consideration rather than that of diagnosis, although dental surgeries are well lit.

In fact, because of the need to have a light source that gives a high luminous energy the hand instruments according to the known art use iodine filament lamps that emit white light.

Said hand instruments according to the prior art have various drawbacks.

In fact, the need to first carry out the operation of diagnosing the areas of plaque and then remove the plaque by means of the hand instrument causes a pointless waste of time and possible lack of precision in the operation because the dentist must necessarily remember the areas of plaque shown up by the blue light.

The white light coming from filament lamps used only for illumination presents a further problem. In fact during the cleaning operation said light, entering into contact with the splashes of cleaning fluid coming from the hole in the workpiece, causes misting which prevents clear visibility.

The object of the invention is to eliminate these drawbacks at the same time providing a hand instrument that is simple to make provided with a light source used for diagnostic purposes.

This object is achieved according to the invention with the characteristics listed in claim 1.

Preferred embodiments of the invention emerge from the dependent claims.

In the hand instrument according to the invention a blue light is used as the light source so that during the plaque removal operation the dentist finds the areas on which to work already highlighted, treated beforehand with a contrast agent, with a consequent higher precision and greater operating speed.

High-efficiency LEDs that transmit blue light, that is with an emission spectrum having a wave length that ranges between 450 nm and 470 nm, can advantageously be used as the light source.

To overcome the problem of illumination of the oral cavity a mixture of light beams of a plurality of LEDs that emit at different frequencies can be employed in order to be able, through the known RGB combination method, to obtain a white light that allows optimal visibility of the oral cavity without the problem of misting.

The LED can be appropriately incorporated into the body of the hand instrument and the same power supply as for the transducer of the hand instrument can be used as the power supply for the LEDs with a consequent reduction in the size of the instrument.

Further characteristics of the invention will be made clearer by the detailed description that follows, referring to a purely exemplary and therefore non-limiting embodiment thereof, illustrated in the appended drawings.

BRIEF DESCRIPTION OF THE DRAWINGS

FIG. 2 shows a partial section of the hand instrument according to the invention with the cover element removed;

FIG. 4 shows an exploded partial section of a further embodiment of the hand instrument according to the invention;

DETAILED DESCRIPTION OF THE PREFERRED EMBODIMENTS

The hand instrument according to the invention will now be described with the aid of the figures.

Figure 1:
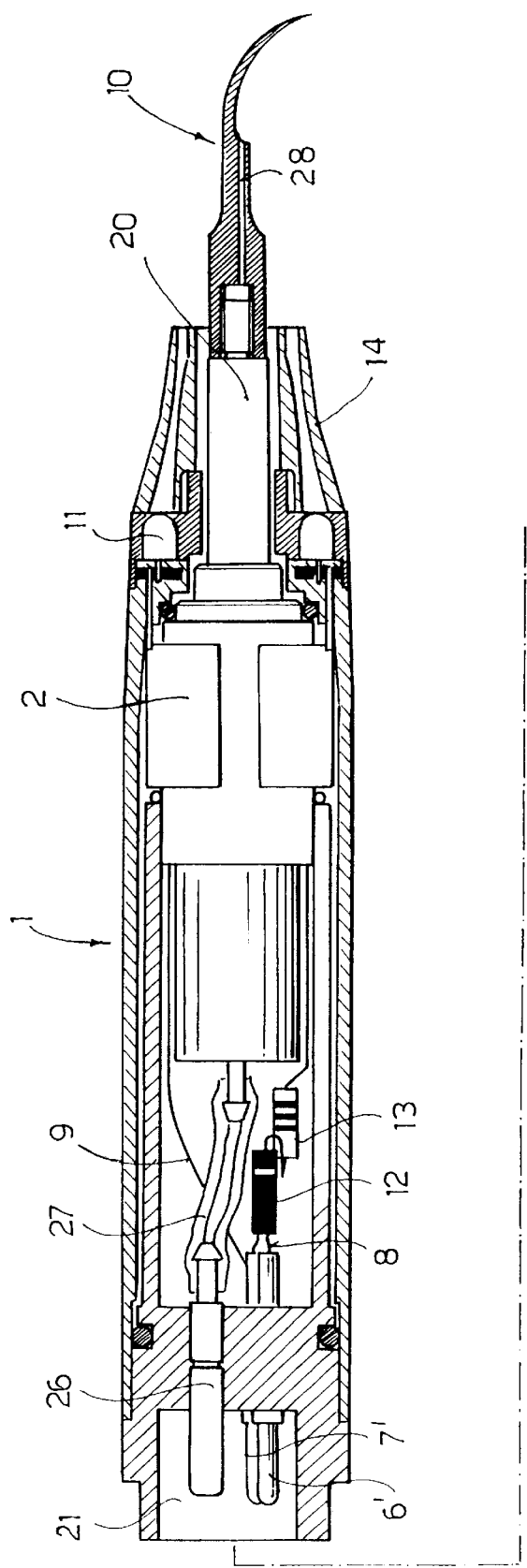
FIG. 1 shows an axial section of the hand instrument according to the invention with the connector element thereof.
Figure 1:
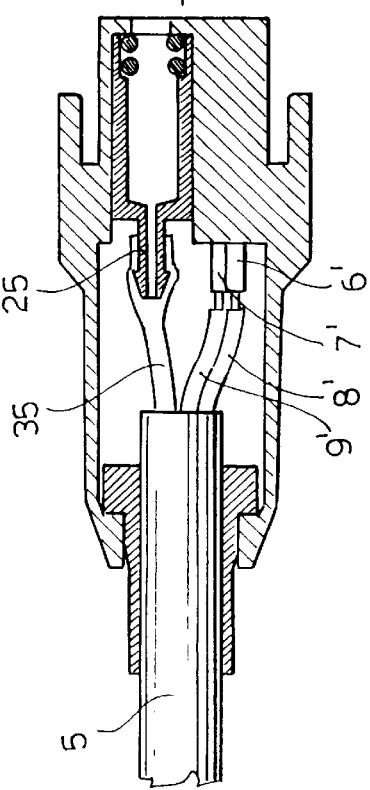

In FIG. 1 a hand instrument consisting of a hollow cylindrical-shaped body 1 can be seen. Inside said body a transducer 2 is positioned. Said transducer consists of a piezoelectric ceramic resonator that is powered in alternating current and acts as a concentrator for sound waves which are transmitted, through a metallic cylindrical arm 20, to a hooked workpiece 10 which by entering into vibration carries out removal of the tartar and plaque from the patient's teeth. A through hole 28 is formed in said workpiece for delivery of the cleaning liquid.

At the end of the body 1 of the hand instrument where the workpiece 10 is connected housings are formed wherein the LEDs 11 are positioned. A truncated conical shaped cover 14 which partially covers the cylindrical arm 20 is coupled to said end allowing the workpiece 10 to protrude. Through cavities are formed in the body of said cover 14 wherein optical fibres or light guides 15 are positioned so that there is a perfect coupling with the light emitting surface of the LEDs 11.

At the other end of the hand instrument is an electrical and hydraulic connector 21 destined to engage with a matching electrical and hydraulic connector 4 that carries an outer sheath 5. A cleaning fluid feed tube 35, an electrical power supply cable 8' and a grounding cable 9' are passed inside said sheath.

Inside the matching connector element 4 the cleaning fluid feed tube 35 is connected to a hydraulic coupling 25, the electrical power cable 8' is connected to an electrical power supply contact 6 and the grounding cable 9' is connected to a contact to earth 7. The hydraulic coupling 25 engages with a hydraulic connector 26 formed in the connector element 21. A tube element 27 is connected to the hydraulic connector 26. Said tube element 27 is used to convey the cleaning fluid inside the body 1 of the hand instrument in such a manner that said fluid can leave the hole 28 formed in the workpiece 10 at an adequate pressure.

The electrical contacts 6, 7 are destined to engage with respective matching contacts 6', 7' formed in the connector 21 integral with the body 1 of the hand instrument. Said contacts 6', 7' are respectively connected to a power supply cable 8 and a grounding cable 9. The power supply cable 8 and the grounding cable 9 are connected to the transducer 2 so as to provide the necessary alternating-voltage power supply.

Figure 5:
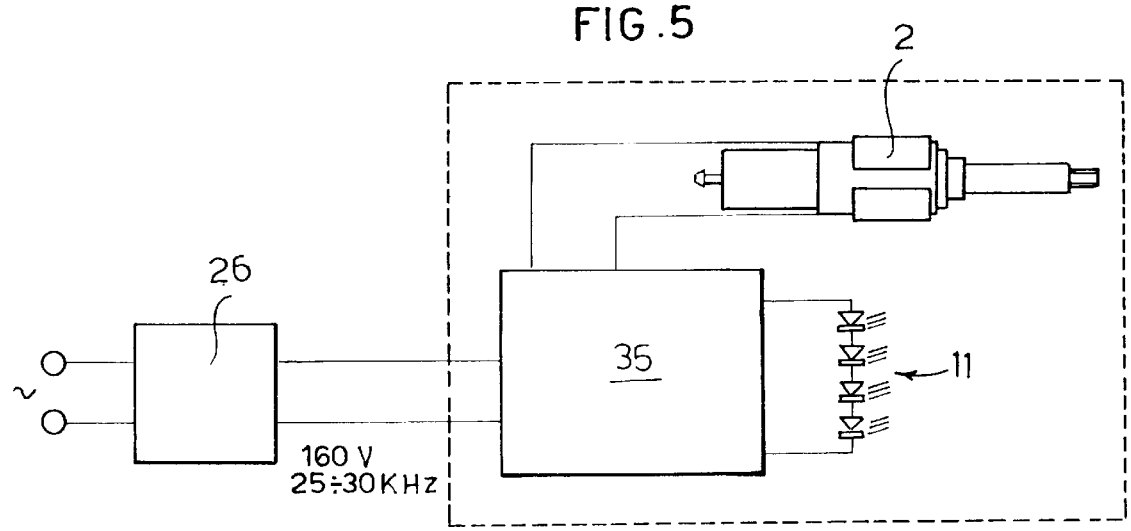
FIG. 5 shows a general wiring diagram of the LED connection circuit.

Polarization of the LEDs 11 can be obtained, for example, using the circuit diagram in FIG. 5. In said diagram the LEDs are connected in series and are polarized through an electronic circuit 35 connected to the power supply cable 8. Said power supply cable 8 comes from a transformer 26 that transforms the line voltage into an alternating 160 Volt r.m.s sinusoidal voltage at a frequency oscillating between 25 KHz and 30 KHz, necessary for the power supply to the piezoelectric ceramic resonator. The electronic circuit can be inductive or capacitive or of another type.

Figure 6:
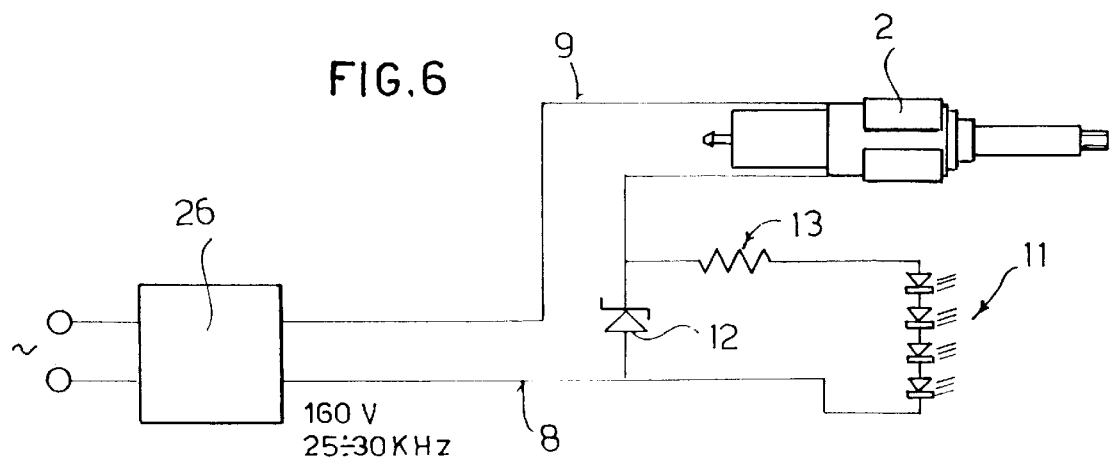
FIG. 6 shows a particular embodiment of the LED connection circuit.

In particular in FIG. 6 a preferred embodiment of the LED polarization circuit is shown. In this case the polarization of the LEDs is obtained by means of a Zener diode 12 in series with a resistance 13 connected to the power supply cable 8.

Figure 3:
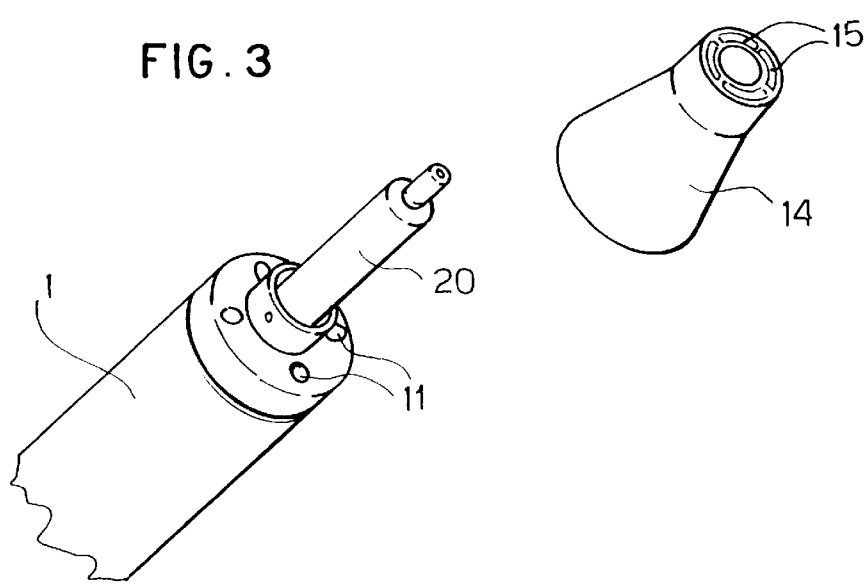
FIG. 3 shows an axonometric view of one end of the hand instrument according to the invention showing a possible type of housing for optical fibres or light guides.

In FIGS. 1 and 3 a preferred embodiment of the invention is presented wherein four LEDs 11 are positioned in their own housings spaced from each other by an angle of about 90° on the circumference of the end of the body 1 of the hand instrument.

Four through cavities are formed in the cover 14 for four optical fibres or light guides 15 destined to be coupled with the four LEDs 11.

In FIG. 4 a further embodiment of the hand instrument according to the invention is shown wherein some LEDs are positioned in a housing formed in the body of the cover 14 and coupled directly with the respective optical fibres or light guides 15. This solution must provide electrical connectors 30 connected to the LEDs 11 that engage with the respective mating electrical connectors 31 connected with a diode polarization circuit inside the body 1 of the hand instrument and supplied by the same power supply as the transducer 2 of the hand instrument.

What is claimed is:

1. A dental hand instrument comprising: a body (1) inside which is positioned a transducer (2) used to vibrate a workpiece (10) in particular serving to remove tartar and plaque from the tooth surface, a cover (14) coupled to said body, a light source to illuminate the work area, and an external connector (4) to provide the electrical power supply to the transducer (2) characterized in that said light source is incorporated in the body (1) of the hand instrument and comprises an LED (11) that emits a blue light able to reveal tartar and/or plaque in the areas in which to operate, previously treated with a contrast agent.

2. A dental hand instrument according to claim 1, characterized in that optical fibres or light guides (15) focus the light emission coming from said light source.

3. A dental hand instrument according to claim 2, characterized in that said optical fibres or light guides (15) are housed in through cavities formed in the cover (14) of the hand instrument.

4. A dental hand instrument according to claim 1, characterized in that it includes a plurality of said LEDs (11) and that said LEDS (11) are connected in series and are polarized through an electronic circuit (35) supplied at a sinusoidal alternating voltage at 160 Volts r.m.s and a frequency oscillating from 25 KHz to 30 KHz.

5. A dental hand instrument according to claim 4, characterized in that said electronic circuit (35) is of the capacitive or inductive type.

6. A dental hand instrument according to claim 4, characterized in that said electronic circuit (35) comprises a Zener diode (12) and a resistance (13) in series.

7. A dental hand instrument comprising: a body (1) inside which is positioned a transducer (2) used to vibrate a workpiece (10) in particular serving to remove tartar and plaque from the tooth surface, a cover (14) coupled to said body, a light source to illuminate the work area, and an external connector (4) to provide the electrical power supply to the transducer (2) characterized in that said light source is incorporated in the body (1) of the hand instrument and emits a blue light able to reveal tartar and/or plaque in the areas in which to operate, previously treated with a contrast agent.

8. A dental hand instrument according to claim 7, characterized in that optical fibres or light guides (15) focus the light emission coming from said light source.

* * * * *